United States Patent
Martin et al.

(10) Patent No.: US 9,248,257 B2
(45) Date of Patent: Feb. 2, 2016

(54) TUNNELER DEVICE AND METHOD OF USE

(75) Inventors: Peter Martin, Assonet, MA (US);
Steven B. Cote, Uxbridge, MA (US);
Dillon Burgess, Cranston, RI (US)

(73) Assignee: Covidien LP, Mansfield, MA (US)

( * ) Notice: Subject to any disclaimer, the term of this patent is extended or adjusted under 35 U.S.C. 154(b) by 553 days.

(21) Appl. No.: 12/894,882

(22) Filed: Sep. 30, 2010

(65) Prior Publication Data
US 2012/0083794 A1   Apr. 5, 2012

(51) Int. Cl.
*A61B 17/00* (2006.01)
*A61M 25/01* (2006.01)
*A61B 17/34* (2006.01)
*A61B 17/32* (2006.01)

(52) U.S. Cl.
CPC ........ *A61M 25/0194* (2013.01); *A61B 17/3415* (2013.01); *A61B 2017/00477* (2013.01); *A61B 2017/320056* (2013.01); *A61B 2017/3456* (2013.01); *A61M 2025/0197* (2013.01)

(58) Field of Classification Search
CPC .............. A61B 17/32; A61B 17/3415; A61B 17/3462; A61B 17/3468; A61B 17/3421; A61B 2012/0046; A61B 2012/00477; A61B 2012/3445; A61B 2012/3456; A61B 2012/320056; A61M 25/01; A61M 25/0102; A61M 25/0194; A61M 2025/0197
USPC ............ 604/164.01, 164.07, 164.09, 164.12, 604/170.01–170.02, 523, 528, 533–534, 604/537, 93.01, 174–175, 264, 506; 606/108, 190–191
See application file for complete search history.

(56) References Cited

U.S. PATENT DOCUMENTS

| | | |
|---|---|---|
| 4,299,228 A | 11/1981 | Peters |
| 4,490,136 A | 12/1984 | Ekbladh et al. |
| 4,674,496 A | 6/1987 | Svadjian et al. |
| 4,705,041 A | 11/1987 | Kim |
| 4,819,694 A | 4/1989 | Jiang |
| 4,832,687 A | 5/1989 | Smith |
| 5,059,170 A | 10/1991 | Cameron |
| 5,129,891 A | 7/1992 | Young |
| 5,207,643 A | 5/1993 | Davis |
| 5,209,723 A | 5/1993 | Twardowski et al. |

(Continued)

FOREIGN PATENT DOCUMENTS

| | | |
|---|---|---|
| CN | 1688352 A | 10/2005 |
| WO | WO 2005/009502 | 2/2005 |

OTHER PUBLICATIONS

Polycath, Polyurethane Central Venous Catheter CVC 100-50, CVC 100-65, CVC 200-60, CVC 200-68.

(Continued)

*Primary Examiner* — Katherine Rodjom
*Assistant Examiner* — Kendra Obu
(74) *Attorney, Agent, or Firm* — John Paul Mello, Esq.

(57) ABSTRACT

A tunneler device is provided. The tunneler device includes a handle formed on a proximal end thereof configured for operable engagement by a user, a shaft extending distally from the handle, a collet supported on the distal end of the shaft, the collet including a plurality of distally extending fingers defining a longitudinal opening, the opening being configured to receive an end of a catheter tube and a connector configured for operable engagement with the collet, wherein the connector is configured to bias the fingers of the collet radially inward upon engagement of the connector with the collet.

16 Claims, 8 Drawing Sheets

(56) References Cited

U.S. PATENT DOCUMENTS

| | | | |
|---|---|---|---|
| 5,279,597 A | 1/1994 | Dassa et al. | |
| 5,358,506 A | 10/1994 | Green et al. | |
| 5,405,320 A | 4/1995 | Twardowski et al. | |
| 5,417,511 A * | 5/1995 | Warden | 403/109.5 |
| 5,478,318 A | 12/1995 | Yoon | |
| 5,505,714 A | 4/1996 | Dassa et al. | |
| 5,509,897 A | 4/1996 | Twardowski et al. | |
| 5,562,618 A | 10/1996 | Cai et al. | |
| 5,613,945 A | 3/1997 | Cai et al. | |
| 5,624,413 A | 4/1997 | Markel et al. | |
| 5,632,729 A | 5/1997 | Cai et al. | |
| 5,637,102 A | 6/1997 | Tolkoff et al. | |
| 5,718,678 A | 2/1998 | Fleming, III | |
| 5,743,873 A | 4/1998 | Cai et al. | |
| 5,944,732 A | 8/1999 | Raulerson et al. | |
| 6,099,519 A | 8/2000 | Olsen et al. | |
| 6,113,572 A | 9/2000 | Gailey et al. | |
| 6,126,631 A | 10/2000 | Loggie | |
| 6,423,053 B1 | 7/2002 | Lee | |
| 6,453,185 B1 | 9/2002 | O'Keefe | |
| 6,638,242 B2 | 10/2003 | Wilson et al. | |
| D498,844 S | 11/2004 | Diamond et al. | |
| 6,858,019 B2 | 2/2005 | McGuckin, Jr. et al. | |
| 6,872,198 B1 | 3/2005 | Wilson et al. | |
| 6,911,014 B2 | 6/2005 | Wentling et al. | |
| 6,916,051 B2 | 7/2005 | Fisher | |
| 6,921,396 B1 | 7/2005 | Wilson et al. | |
| 6,939,328 B2 | 9/2005 | Raulerson | |
| 6,969,381 B2 | 11/2005 | Voorhees | |
| 6,979,339 B2 | 12/2005 | Bishop et al. | |
| 7,008,395 B1 | 3/2006 | Loggie | |
| 7,087,071 B2 | 8/2006 | Nicholas et al. | |
| 7,128,734 B1 | 10/2006 | Wilson et al. | |
| 7,144,409 B2 | 12/2006 | Aranyi | |
| 7,163,531 B2 | 1/2007 | Seese et al. | |
| 7,261,708 B2 | 8/2007 | Raulerson | |
| 7,300,430 B2 | 11/2007 | Wilson et al. | |
| 7,377,915 B2 | 5/2008 | Rasmussen et al. | |
| 8,105,313 B2 * | 1/2012 | Schweikert et al. | 604/533 |
| 8,137,316 B2 * | 3/2012 | Haarala et al. | 604/164.01 |
| 2004/0034324 A1 | 2/2004 | Seese et al. | |
| 2004/0065333 A1 | 4/2004 | Wilson et al. | |
| 2004/0167478 A1 | 8/2004 | Mooney et al. | |
| 2004/0171997 A1 | 9/2004 | Wilson et al. | |
| 2004/0176739 A1 | 9/2004 | Stephens et al. | |
| 2005/0027282 A1 * | 2/2005 | Schweikert et al. | 604/523 |
| 2005/0085765 A1 | 4/2005 | Voorhees | |
| 2005/0107770 A1 | 5/2005 | Schweikert et al. | |
| 2005/0137580 A1 | 6/2005 | Raulerson et al. | |
| 2005/0209581 A1 * | 9/2005 | Butts et al. | 604/523 |
| 2005/0209583 A1 | 9/2005 | Powers et al. | |
| 2005/0209584 A1 | 9/2005 | Rome | |
| 2005/0228364 A1 | 10/2005 | Braga | |
| 2005/0256461 A1 | 11/2005 | DiFiore et al. | |
| 2005/0261665 A1 | 11/2005 | Voorhees | |
| 2006/0009783 A1 | 1/2006 | Rome et al. | |
| 2006/0015086 A1 | 1/2006 | Rasmussen et al. | |
| 2006/0015130 A1 | 1/2006 | Voorhees, Jr. et al. | |
| 2006/0095062 A1 | 5/2006 | Stephens | |
| 2006/0135949 A1 | 6/2006 | Rome et al. | |
| 2006/0224110 A1 | 10/2006 | Scott et al. | |
| 2006/0276773 A1 | 12/2006 | Wilson et al. | |
| 2007/0016167 A1 | 1/2007 | Smith et al. | |
| 2007/0049960 A1 | 3/2007 | Stephens et al. | |
| 2007/0060866 A1 | 3/2007 | Raulerson et al. | |
| 2007/0078396 A1 | 4/2007 | Feeley et al. | |
| 2007/0260221 A1 | 11/2007 | Chesnin | |
| 2007/0265597 A1 | 11/2007 | Schweikert et al. | |
| 2007/0282274 A1 | 12/2007 | Chesnin | |
| 2008/0009832 A1 * | 1/2008 | Barron et al. | 604/533 |
| 2008/0086161 A1 | 4/2008 | Massengale et al. | |
| 2008/0097409 A1 | 4/2008 | Stephens | |
| 2008/0214991 A1 * | 9/2008 | Haarala et al. | 604/43 |
| 2008/0214992 A1 | 9/2008 | Haarala | |
| 2009/0137944 A1 | 5/2009 | Haarala et al. | |
| 2010/0063512 A1 * | 3/2010 | Braga et al. | 606/108 |

OTHER PUBLICATIONS

"Aspira*Pleural Drainage System", Bard Access Systems, Inc., Salt Lake City, Utah, Instruction Manual dated Oct. 2007.
"Aspira*Pleural Drainage Catheter", Bard Access Systems, Inc., Product Description and Instruction Manual (undated).
"Aspira*Pleural Drainage System—Compassionate Treatment", Bard Access Systems, Inc., Product Description Article (undated).
"Aspira*Pleural Drainage System Product Features", Bard Access Systems, from website http://www.myaspira.com/pages/clinchoose.html.
European Patent Search Report EP 11 18 3344 dated Dec. 21, 2011.
Third Office Action, and translation thereof, from Counterpart Chinese Patent Application No. 201110361788.5, dated Nov. 19, 2014, 19 pp.
Examination Report from counterpart European Application No. 11183344.8, dated Jun. 22, 2015, 3 pp.
Notice of Reasons for Rejection, and translation thereof, from counterpart Japanese Application No. 2011-215388, dated Feb. 19, 2013, 4 pp.
Second Office Action, and translation thereof, from counterpart Chinese Application No. 201110361788.5, dated Jun. 5, 2014, 22 pp.
Examination Report from counterpart European Patent Application No. 11183344.8, dated Sep. 30, 2013, 4 pp.

* cited by examiner

TUNNELER DEVICE AND METHOD OF USE

BACKGROUND

1. Technical Field

The present disclosure relates to indwelling catheters. More particularly, the present disclosure relates to a tunneler device for subcutaneously tunneling a catheter under a patient's skin.

2. Background of Related Art

Catheters are flexible instruments intended for the withdrawal and introduction of fluids relative to body cavities, ducts, and vessels. Typically, a distal end of the catheter is implanted into, for example, the vasculature of a patient to withdraw blood or introduce medicaments. When a catheter assembly is implanted into the vasculature of a patient, the catheter's distal portion is inserted through an incision in the patient's skin and into the vasculature (venotomy site) until the distal tip is precisely located at the desired site, while the proximal portion remains external of the patient for access to the catheter for infusion and/or withdrawal of fluids such as for hemodialysis. The proximal portion may simply extend from the venotomy site and be secured to the patient. Alternatively, the proximal portion may be tunneled under the patient's skin to a site remote from the venotomy site using known procedures. To tunnel the proximal portion of the catheter under the patient's skin, tunneler devices are typically secured to the proximal portion of the catheter to pull the catheter under the patient's skin from the venotomy site to the remote site.

Tunneler devices have one end which is configured to securely engage the proximal end of the catheter. Typically, the engagement end of the tunneler device includes at least one prong which is dimensioned to be received within a lumen or lumens of the catheter. Although this provides somewhat effective connection of the tunneler device to the catheter, detachments are known to occur during a subsequent tunneling procedure. Such detachments may prolong the procedure and require the use of a second tunneler, thereby increasing the cost of the procedure.

Therefore, it would be beneficial to have a tunneling device including a catheter securement device which is capable of improved securement of the tunneler device to the catheter to prevent detachment during a tunneling procedure.

SUMMARY

Accordingly a tunneler device is provided. In general, in one aspect of the present disclosure, a tunneler device includes a handle formed on a proximal end thereof configured for operable engagement by a user, a shaft extending distally from the handle, a collet supported on the distal end of the shaft, the collet including a plurality of distally extending fingers defining a longitudinal opening, the opening being configured to receive an end of a catheter tube and a connector configured for operable engagement with the collet, wherein the connector is configured to bias the fingers of the collet radially inward upon engagement of the connector with the collet.

In one embodiment, the collet includes four (4) fingers. Each of the plurality of fingers may include at least one radially inward extending prong. At least one radially inward extending prong may be configured to frictionally engage an outside surface of the catheter tube received within the longitudinal slot. The connector may be configured for threaded engagement with the collet. The tunneler device may further include a cap configured for selective engagement with the collet. The cap may be configured for threaded engagement with the collet. The cap may further be configured for blunt tissue dissection. In one embodiment, the cap includes longitudinally extending ribs. The shaft may include a first shaft portion at an angle relative to a second shaft portion and the angle between the first shaft portion and the second shaft portion may be thirty degrees (30°).

In general, in another aspect of the present disclosure, a tunneler device includes a handle formed on a proximal end thereof configured for operable engagement by a user, a shaft extending distally from the handle, a collet supported on the distal end of the shaft, the collet including a plurality of distally extending fingers and a longitudinal projection radially spaced from the fingers, the projection being configured to be received within a lumen of a catheter tube and a connector configured for operable engagement with the collet, wherein the connector is configured to bias the fingers of the collet radially inward towards the longitudinal projection upon engagement of the connector with collet. The tunneler device may further include a cap configured for selective engagement with the collet. The cap may be configured for blunt tissue dissection.

In general, in yet another aspect of the present disclosure, a tunneler device includes a handle formed on a proximal end thereof configured for operable engagement by a user, a shaft extending distally from the handle, a collet supported on the distal end of the shaft, the collet including a plurality of distally extending fingers and a longitudinal projection radially spaced from the fingers, the projection being configured to be received within a lumen of a catheter tube and each of the plurality of fingers including at least one radially inward extending prong, a connector configured for operable engagement with the collet, wherein the connector is configured to bias the fingers of the collet radially inward towards the longitudinal projection upon engagement of the connector with collet to frictionally engage the catheter tube between the fingers and the projection and a cap configured for selective engagement with the collet, wherein the cap is configured for blunt tissue dissection.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

The embodiments of the present disclosure are directed to a tunneling system incorporating a connector adapted for interconnecting an elongate tunneling member and a catheter. The tunneling system of the present disclosure may have various medical applications. During a hemodialysis catheter implantation procedure, the tunneling system creates or enlarges a subcutaneous tunnel within a subject and positions a catheter in the target site. It is envisioned, however, that the presently disclosed tunneling system may be employed in any other suitable procedure. For instance, the tunneling system of the present disclosure may be utilized for subcutaneously implanting vascular devices such as stents, vascular grafts, or the like, inside a subject's body.

In the discussion that follows, the term "clinician" refers to a doctor, a nurse, or any other care provider and may include support personnel. The term "proximal" refers to the portion of a structure that is closer to a clinician, whereas the term "distal" refers to the portion that is farther from the clinician.

Figure 1:
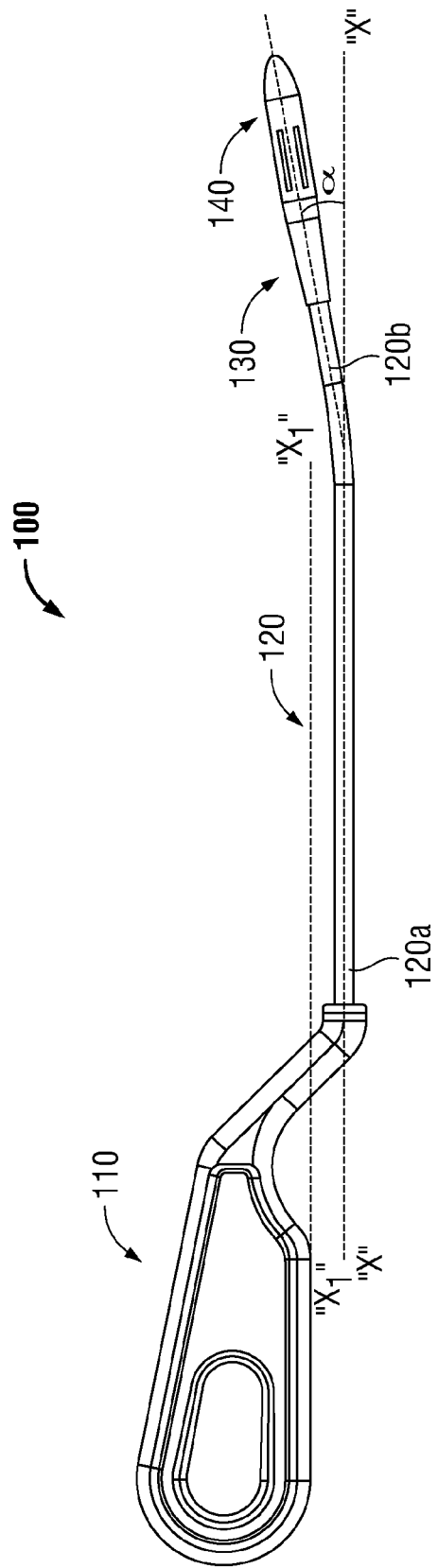
FIG. 1 is a side view of an embodiment of the tunneler device according to the present disclosure, with a cap secured to the distal end of the tunneler device.
Figure 2:
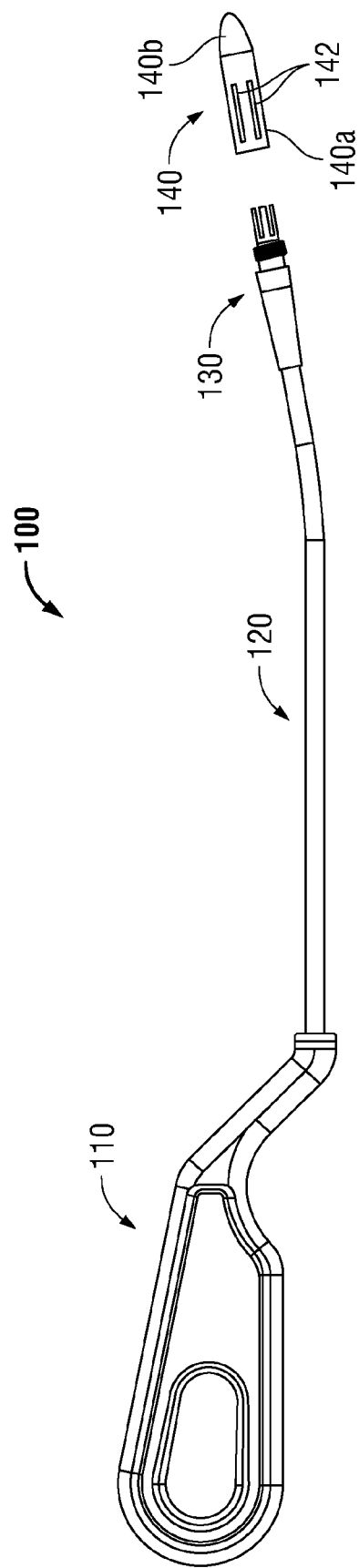
FIG. 2 is a side view of the tunneler device of FIG. 1, with the cap removed from the distal end of the tunneler device.

With reference to FIGS. 1 and 2, a tunneler device according to the present disclosure is shown generally as tunneler device 100. Although tunneler device 100 will be described for use in the placement of a dialysis catheter, it is envisioned that tunneler device 100 may be used for the placement of various other medical implements. Tunneler device 100 includes a handle 110, a shaft 120 extending from handle 110, a collet 130 mounted on a distal end 120b of shaft 120 and a cap 140 selectively engagable with collect 130. Any or all of the components of tunneler device 100 may be sterilizable, and thus, reusable. Alternatively, tunneler device 100 may be disposable.

Still referring to FIGS. 1 and 2, handle 110 is formed on a proximal end 120a of tunneler device 100 and is configured for operable engagement by a user. Handle 110 may be formed of plastic, polymer or other suitable material and may be coated or include ridges, bumps or knurls, or may otherwise be configured to facilitate engagement by a user to manipulate the tunneler device 100. Handle 110 may also be configured for operable engagement with a robotic arm (not shown) or other manipulating device.

Shaft 120 of tunneler device 100 extends distally from handle 110 and defines a longitudinal axis "X" extending along a proximal portion 120a thereof. A seen in FIG. 2, handle 110 may define a gripping axis "$X_1$", laterally spaced from longitudinal axis "X". The laterally separation between handle 110 and proximal portion 120a of shaft 120 may enable greater manipulation of tunneler device 100 during a catheter implantation procedure.

Still referring to FIGS. 1 and 2, distal portion 120b of shaft 120 may extend at an angle "α" relative to longitudinal axis "X". Angle "α" may be between zero and sixty degrees (0-60°). The degree of angulation may vary depending on the desired location of the tunnel to be formed. Further, the shaft 120 may be malleable to enable the clinician to bend the shaft as needed for a particular procedure. For example, the clinician may bend the shaft 120 into a curved shape to enable the tunneler device 100 to create a curved or arced tunnel. Distal portion 120b of shaft 120 includes a collet 130 configured for selective engagement with a cap 140 and a connector 150, shown in FIG. 3. Collet 130 may be integrally formed with shaft 120, or, in the alternative, secured to shaft 120 such as by overmolding With particular reference now to FIG. 3, collet 130 includes a base 132, an externally threaded portion 134 and a set of longitudinally extending fingers 136 that are flexible and resilient. Although shown to include four (4) fingers 136, it is envisioned that collet 130 of tunneler device 100 may have more or less than four (4) fingers 136. For example, collet 130 may include only a single pair of fingers 136. Threaded portion 134 is configured for threaded engagement with each of cap 140 (FIG. 2) and connector 150 (FIG. 4). Fingers 136 define a longitudinal opening 135 sized and dimensioned to receive a proximal end of a tube 52 that forms at least a part of a catheter 50 (FIG. 4). Each of fingers 136 may also include a prong 138 extending radially into longitudinal opening 135 defined by fingers 136. Each of radially extending prongs 138 is configured for selective engagement with catheter 50, as will be described in further detail below. Although shown to include only single prongs 138 of the same size and configuration, it is envisioned that each of fingers 136 may include multiple prongs 138 of the same or differing sizes and configurations. Prongs 138 may be coated with rubber or include other friction increasing coating materials or configurations, e.g., knurling, to facilitate a more secure engagement of collet 130 with the end of tube 52 of catheter 50 during catheter implantation.

With reference to FIG. 2, cap 140 may include a substantially bullet shaped body having an internally threaded proximal end 140a and a substantially rounded distal end 140b. Internally threaded proximal end 140a of cap 140 is configured for threaded engagement with externally threaded portion 134 of collet 130. Although cap 140 and collet 130 are shown configured for threaded engagement, it is envisioned that other means of securing cap 140 to collet 130 may be utilized. For example, cap 140 may be secured to collet 130 using a bayonet coupling or friction fit. Distal end 140b of cap 140 is configured to be inserted through tissue and may operate as a tissue dissector or expander. Cap 140 may be provided in various sizes for creating tunnels of different sizes. In this manner, tunneler device 100 may be used for the implantation of catheters 50 having different sizes. Cap 140 may include longitudinal ribs 142 extending along at least a portion of a length thereof. Ribs 142 may be configured to facilitate engagement and manipulation of cap 140 by a clinician during placement of cap 140 on collet 130 and during removal of cap 140 therefrom.

Figure 3:
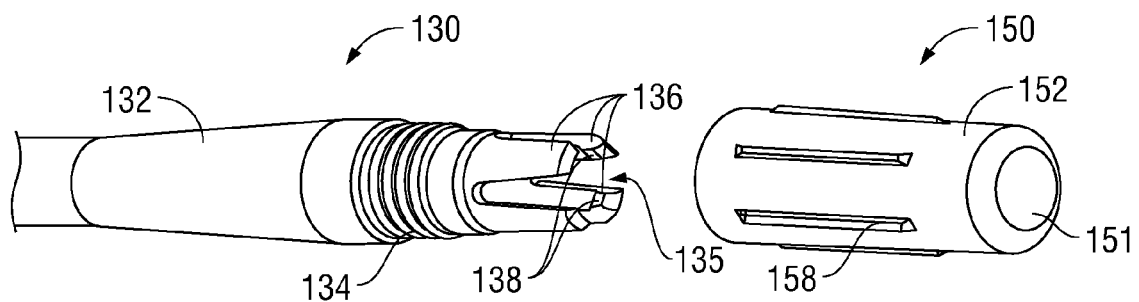
FIG. 3 is an enlarged perspective view of a distal end of the tunneler device shown in FIG. 2.
Figure 4:
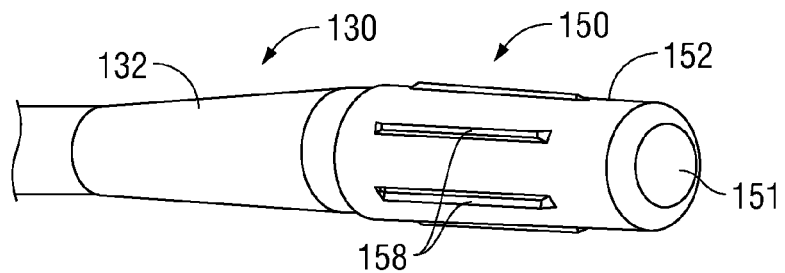
FIG. 4 is enlarged perspective view of the distal end of the tunneler device of FIG. 1.
Figure 5:
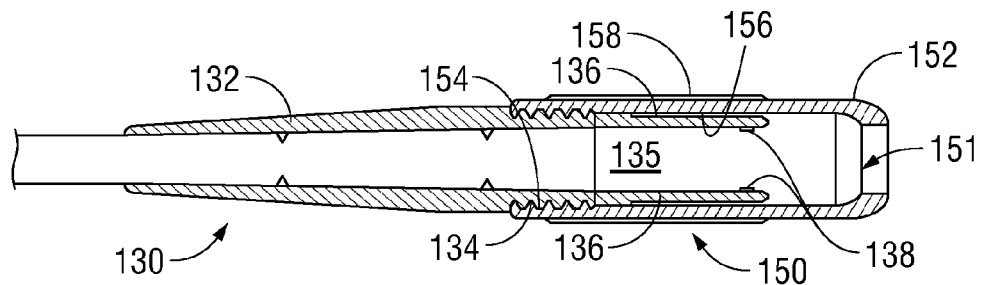
FIG. 5 is a cross-sectional side view of the engagement of the distal end of the tunneler of FIG. 4.
Figure 6:
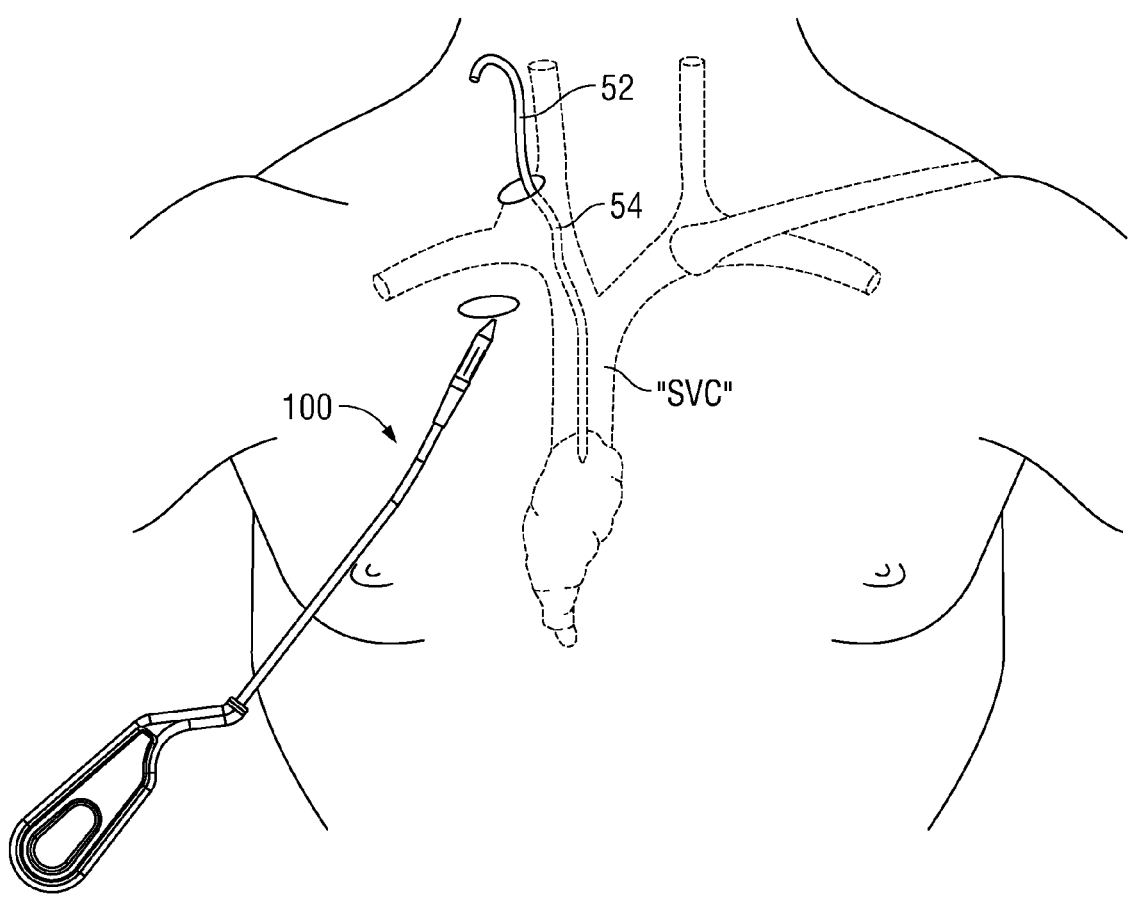
FIG. 6 is a schematic of an upper torso of a patient prior to insertion of the tunneler device of FIG. 1 through an incision.
Figure 7:
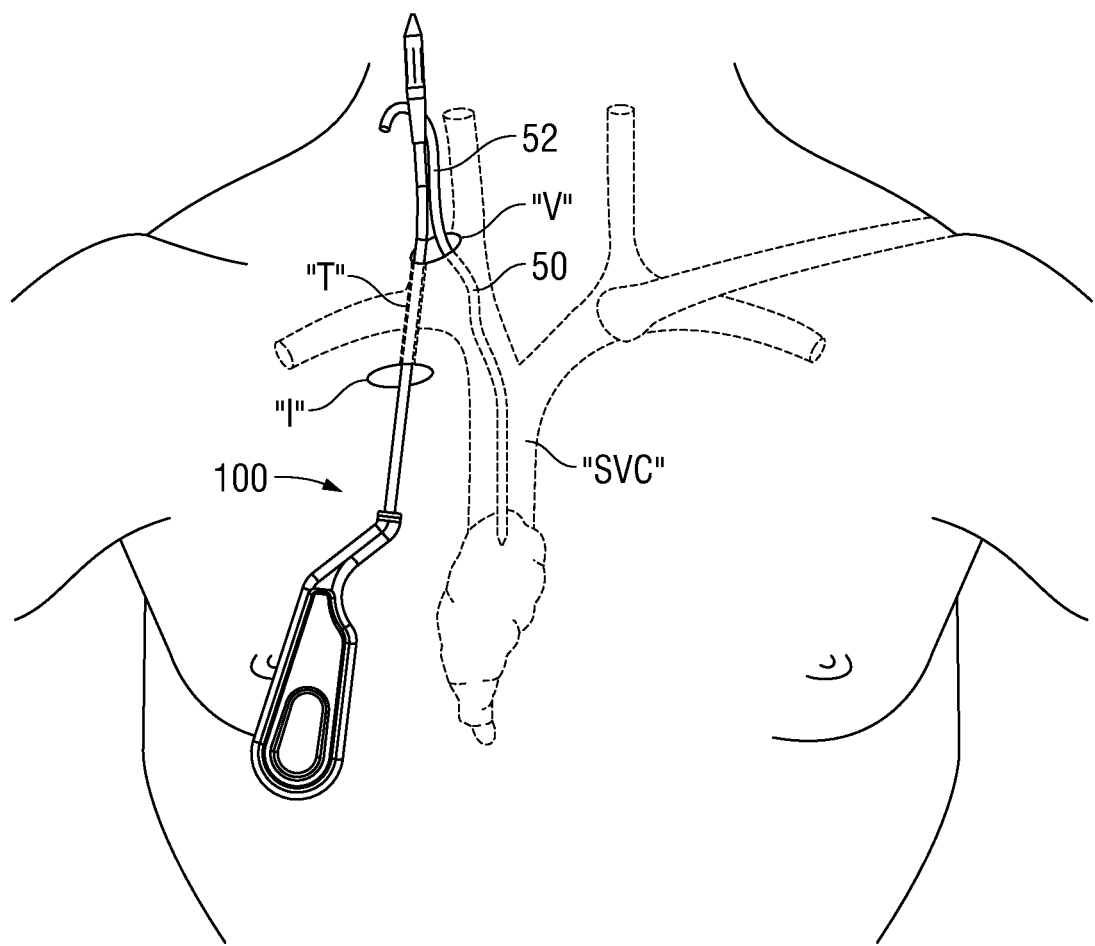
FIG. 7 is a schematic of the upper torso of FIG. 6 subsequent to insertion of the tunneler device of FIG. 1 through the incision.

With reference now to FIGS. 3-5, connector 150 is configured to secure a proximal end of tube 52 (FIG. 8) of catheter 50 to tunneler device 100 by compressing fingers 136 radially inward. Connector 150 defines a substantially cylindrical member 152 defining a passageway 151 therethrough. Passageway 151 is configured to receive tube 52 of catheter 50. Connector 150 includes an internally threaded portion 154 and an internally tapered portion 156 proximal to internally threaded portion 154. Tapered portion 156 is configured to receive longitudinally extending fingers 136 formed on collet 130. As will be discussed in further detail below, tapered portion 156 is configured such that fingers 136 of collet 130 are progressively compressed radially inward as connector 150 is threaded onto collet 130. In this manner, a catheter tube 52 (FIG. 8) extending into opening 135 formed by fingers 136 is radially compressed and frictionally engaged by fingers 136, and prongs 138 if included. Threaded portion 154 is configured to securely engage threaded portion 134 of collet 130. Although connector 150 and collet 130 are shown to be configured for threaded engagement, it is envisioned that other means of securing connector 150 to collet 130 may be utilized. For example, connector 150 may be secured to collet 130 using a bayonet coupling. As with cap 140, connector 150 may also include longitudinal ribs 158. The connector 150 may have an outside diameter substantially similar or equal to an outside diameter of base 132 of collet 130. Such a configuration may provide a smooth transition and outer surface between the connector 150 and the collet 130 so as to help alleviate the tunneler device 100 from getting caught on tissue as the tunneler device 100 is pulled through the tissue.

Figure 11:
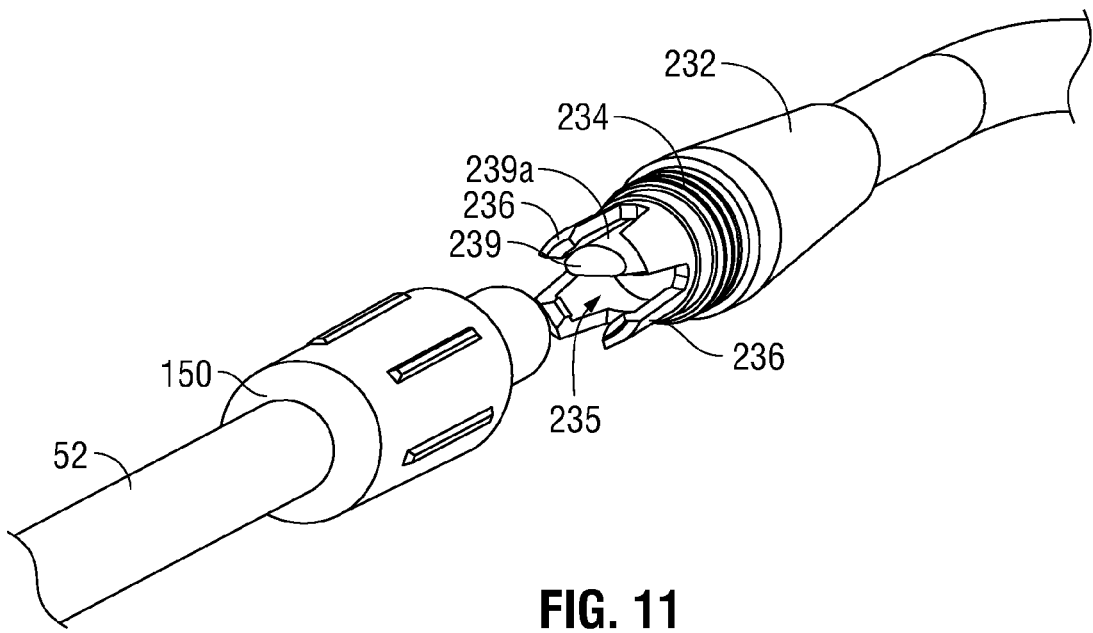
FIG. 11 is a perspective view of the distal end of an alternative embodiment of a tunneler device according to the present disclosure.
Figure 12:
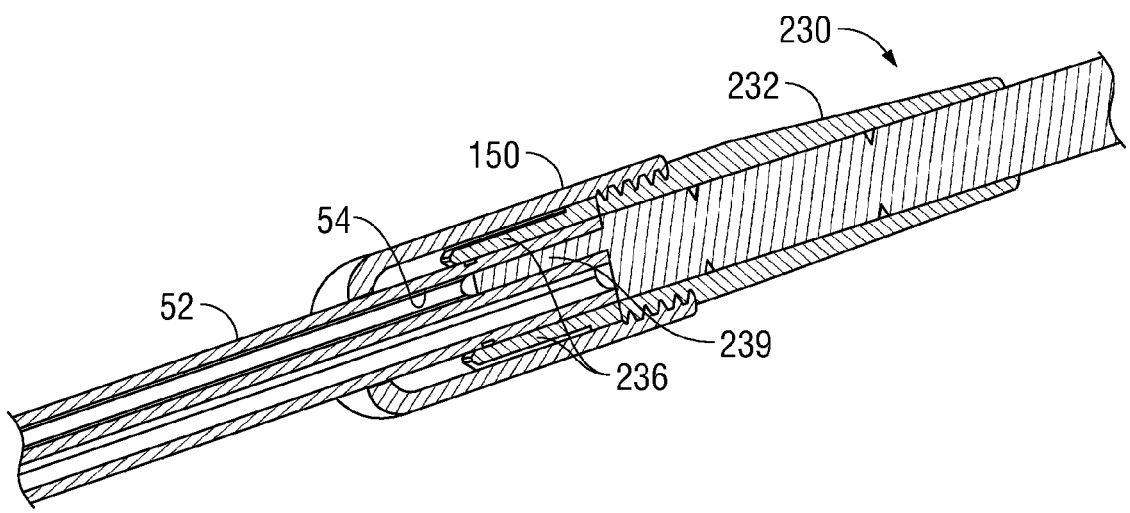
FIG. 12 is a cross-sectional side view of the engagement of the distal end of the tunneler of FIG. 11.

Referring now to FIGS. 11 and 12, an alternative embodiment of collet 130 is shown generally as collet 230. Collet 230 is substantially similar to collet 130, and therefore, will only be described as relates to the differences therebetween. Collet 230 includes a base 232, an externally threaded portion 234 and a set of longitudinally extending fingers 236 defining a longitudinal opening 235 sized and dimensioned to receive a proximal end of a tube 52. Collet 230 further includes a longitudinal projection 239 radially spaced from fingers 236 within passageway 235. Longitudinal projection 239 is configured to engage the inside of tube 52 while one or more of fingers 236 engages an outer surface of tube 52 adjacent longitudinal projection 239. In this manner, fingers 236 and projection 239 operate together to trap tube 52 therebetween and firmly hold catheter 50.

Still referring to FIGS. 11 and 12, projection 239 may include a catheter engaging surface 239a which may be either smooth or barbed. Projection 239 may be sized and dimensioned for reception in one or more lumen 54 of tube 52. In one embodiment, projection 239 includes a diameter slightly greater than that of lumen 54 of tube 52. In this manner, reception of projection 239 within lumen 54 causes expansion of tube 52, thereby increasing the frictional engagement between collect 230 and tube 52. Alternatively, projection 239 is sized to be received within the lumen of tube 52 without deforming tube 52, which may enable a smaller overall collet dimension. It is envisioned that collet 230 may include one or more longitudinal projections 239 for more securely retaining tube 52.

The use of tunneler device 100 will now be described with respect to an exemplary procedure, referring to FIGS. 6-10B. A similar tunneling procedure is described in commonly owned U.S. patent application Ser. No. 11/986,861, filed Nov. 27, 2007, the disclosure of which is hereby incorporated by reference in its entirety. In use, after catheter 50 has been positioned into a patients' vasculature, for example, the superior vena cava "SVC", such that the proximal end of catheter 50 extends from the venotomy site "V", a subcutaneous tunnel is formed between the venotomy site and a position adjacent the clavicle. To accomplish this, an incision "I" is first made adjacent the clavicle. Next, the distal end of tunneler device 100, with cap 140 attached, is inserted through incision "I" and pushed through the tissue to venotomy site "V" to create tunnel "T". Thereafter, cap 140 is removed from the distal end of tunneler device 100.

Figure 8:
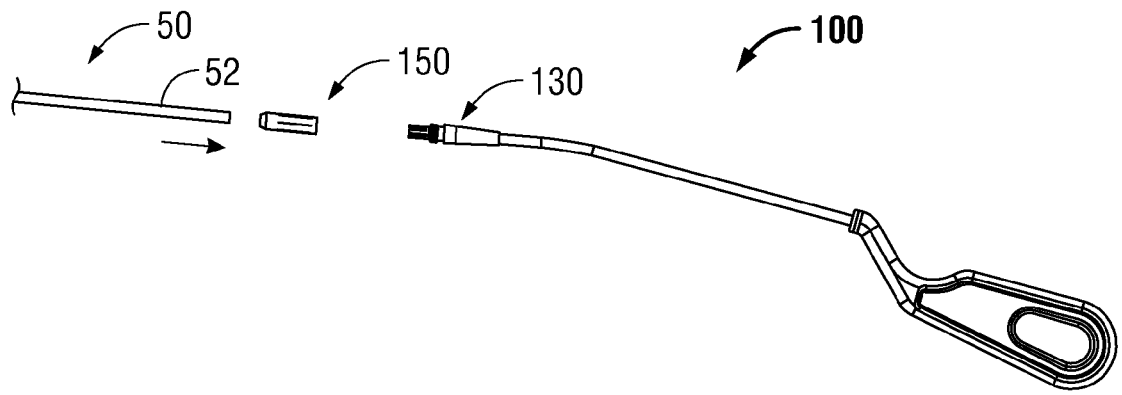
FIG. 8 is a side view of the tunneler device of FIG. 1, prior to reception of a catheter tube in a distal end thereof.
Figure 9A:
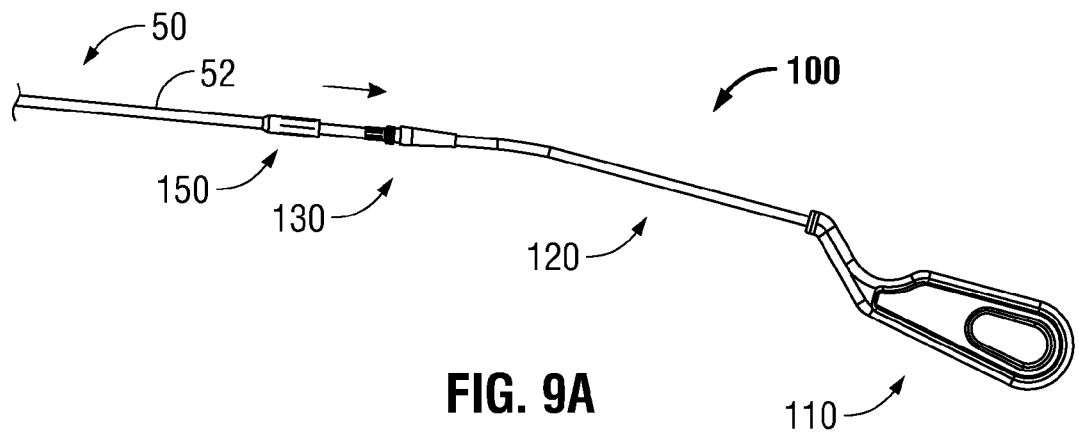
FIG. 9A is a side view of the tunneler device of FIG. 8, with the catheter tube received within the collet at the distal end of the tunneler device.
Figure 10A:
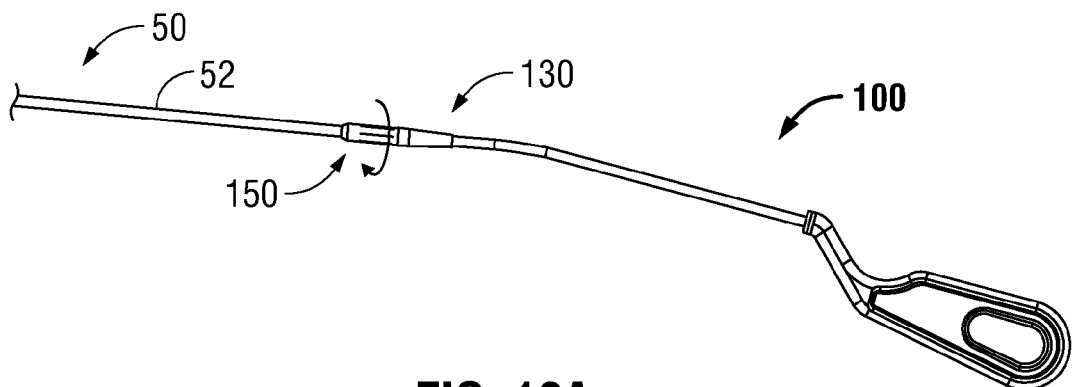
FIG. 10A is a side view of the tunneler device of FIGS. 8 and 9, in secure engagement with the catheter tube.
Figure 9B:
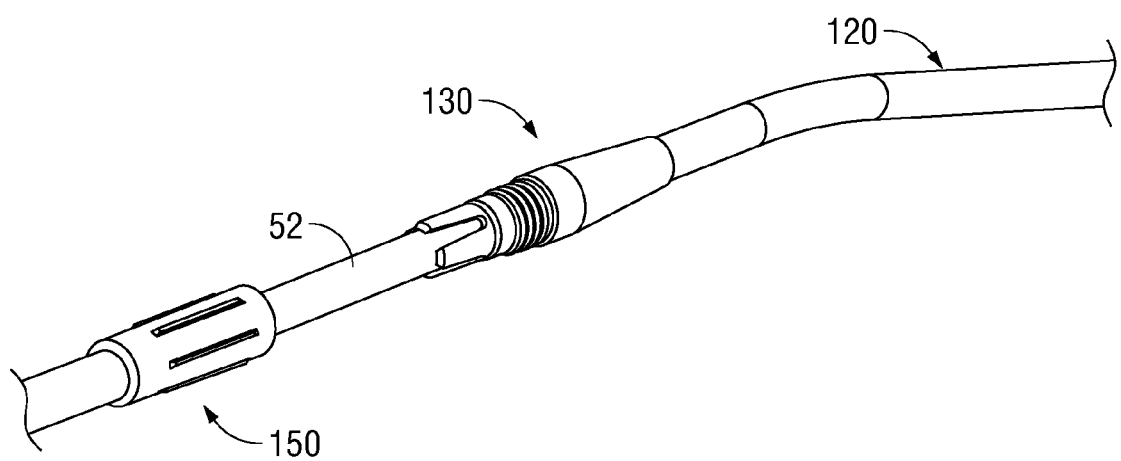
FIG. 9B is a perspective view of the catheter tube received within the collet shown in FIG. 9A.
Figure 10B:
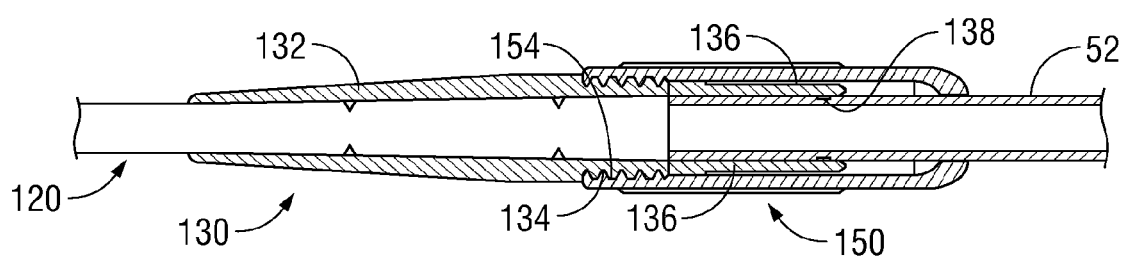
FIG. 10B is a perspective view of the secure engagement of the catheter tube with the tunneler device shown in FIG. 10A.

After the distal end of tunneler device 100 is positioned extending from venotomy site "V" such that collet 130 is exposed, an end of catheter tube 52 is received through passage 151 of connector 150 and inserted into longitudinal opening 135 formed by fingers 136 of collet 130. Turning to FIGS. 8, 9A and 9B, after receiving an end of catheter tube 52 in opening 135 of collet 130, connector 150 is slid over catheter tube 52 and into engagement with collet 130. With reference to FIGS. 10A and 10B, rotation of connector 150 relative to collect 130 causes threaded engagement of internally threaded portion 154 (FIG. 5) of connector 150 with externally threaded portion 134 of collet 130. Progressive engagement of threaded portions 134, 154 causes longitudinally extending fingers 136 of collet 130 to engage tapered portion 156 of connector 150. As fingers 136 engage tapered portion 156, fingers 136 are progressively biased radially inward, which securely engages an outer surface of catheter tube 52.

Once catheter tube 52 is secured to tunneler device 100 through the engagement of collet 130 and connector 150, tunneler device 100 is retracted through tunnel "T". Once completely retracted from tunnel "T", connector 150 is disengaged from collet 130 and catheter tube 52 is removed from within longitudinal opening 135 formed by fingers 136 of collet 130. Alternatively, the tube 52 may be cut to disengage the tunneler device 100 from the rest of the tube 52. As discussed above, any or all of tunneler device 100 may be disposable or sterilizable and reusable.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A tunneler device comprising:
    a handle configured for operable engagement by a user;
    a shaft extending distally from the handle;
    a collet supported on a distal end of the shaft, the collet including a plurality of distally extending fingers defining a longitudinal opening, the opening being configured to receive an end of a catheter tube;
    a cylindrical connector defining a passageway dimensioned to slidably receive the catheter tube, the connector configured for operable engagement with the collet, wherein the connector includes a tapered portion biasing the fingers of collet radially inward when the connector slides over the catheter from a first position on an outer surface of the catheter tube spaced from the collet to a second position threadably engaged with the collet, the tapered portion contacting a length of an outer surface of the fingers to bias the fingers radially inward into engagement with an outer surface of the catheter tube as the connector slides from the first position to the second; and
    a cap configured for selective engagement with the collet.

2. The tunneler device of claim 1, wherein the collet includes four (4) fingers.

3. The tunneler device of claim 1, wherein each of the plurality of fingers includes at least one radially inward extending prong.

4. The tunneler device of claim 3, wherein the at least one radially inward extending prong is configured to frictionally engage the outside surface of the catheter tube received within the longitudinal opening.

5. The tunneler device of claim 1, wherein the cap is configured for threaded engagement with the collet.

6. The tunneler device of claim 1, wherein the cap is configured for blunt tissue dissection.

7. The tunneler device of claim 1, wherein the cap includes longitudinally extending ribs.

8. The tunneler device of claim 1, wherein the shaft includes a first shaft portion at an angle relative to a second shaft portion.

9. The tunneler device of claim 8, wherein the angle between the first shaft portion and the second shaft portion is thirty degrees (30°).

10. A tunneler device comprising:
a handle configured for operable engagement by a user;
a shaft extending distally from the handle;
a collet supported on a distal end of the shaft, the collet including a plurality of distally extending fingers and a longitudinal projection radially spaced from the fingers, the projection being configured to be received within a lumen of a catheter tube;
a cylindrical connector defining a passageway dimensioned to slidabely receive the catheter tube, the connector for operable engagement with the collet, wherein the connector includes a tapered portion biasing the fingers of the collet radially inward towards the longitudinal projection when the connector slides over the catheter from a first position on an outer surface of the catheter tube spaced from the collet to a second position threadably engaged with the collet, the tapered portion contacting a length of an outer surface of the fingers to bias the fingers radially inward into engagement with an outer surface of the catheter tube as the connector slides from the position to the second position; and
a cap configured for selective engagement with the collet.

11. The tunneler device of claim 10, wherein the fingers and longitudinal projection operate to frictionally engage the catheter tube therebetween.

12. The tunneler device of claim 10, wherein the collet includes four (4) fingers.

13. The tunneler device of claim 10, wherein each of the plurality of fingers includes at least one radially inward extending prong.

14. The tunneler device of claim 13, wherein the at least one radially inward extending prong frictionally engages an outside surface of the catheter tube received within a longitudinal opening definded by the plurality of distally extending fingers.

15. The tunneler device of claim 10, wherein the cap is configured for blunt tissue dissection.

16. A tunneler device comprising:
a handle configured for operable engagement by a user;
a shaft extending distally from the handle;
a collet supported on a distal end of the shaft, the collet including a plurality of distally extending fingers and a longitudinal projection radially spaced from the fingers, the projection being configured to be received within a lumen of a catheter tube, and each of the plurality of the distally extending fingers including at least one radially inward extending prong;
a connector configured for operable engagement with the collet, wherein the connector is configured to bias the fingers of the collet radially inward towards the longitudinal projection upon engagement of the connector with collet to frictionally engage the catheter tube between the fingers and the projection, an inner surface of the connector contacting a length of an outer surface of fingers to bias the fingers radially inward into engagement with an outer surface of the catheter tube as the connector slides into threaded engagement with the collet to secure the catheter tube between the fingers and the projection; and
a cap configured for selective engagement with the collet, wherein the cap is configured for blunt tissue dissection.

* * * * *